United States Patent
Lemieux

(10) Patent No.: US 8,688,224 B2
(45) Date of Patent: *Apr. 1, 2014

(54) IMPLANTABLE BIOMEDICAL DEVICE INCLUDING AN ELECTRICAL ENERGY GENERATOR

(75) Inventor: Aaron Patrick Lemieux, Cleveland, OH (US)

(73) Assignee: Tremont Electric, Inc., Cleveland, OH (US)

( * ) Notice: Subject to any disclaimer, the term of this patent is extended or adjusted under 35 U.S.C. 154(b) by 371 days.

This patent is subject to a terminal disclaimer.

(21) Appl. No.: 12/399,448

(22) Filed: Mar. 6, 2009

(65) Prior Publication Data

US 2009/0281600 A1 Nov. 12, 2009

Related U.S. Application Data

(60) Provisional application No. 61/034,651, filed on Mar. 7, 2008.

(51) Int. Cl.
*A61N 1/02* (2006.01)
(52) U.S. Cl.
USPC .................................................. 607/61
(58) Field of Classification Search
USPC .................................................. 607/61
See application file for complete search history.

(56) References Cited

U.S. PATENT DOCUMENTS

| | | | |
|---|---|---|---|
| 1,275,514 A | 8/1918 | Wolak | |
| 3,100,292 A | 8/1963 | Warner, Jr. et al. | |
| 3,103,603 A | 9/1963 | Reutter | |
| 3,129,347 A | 4/1964 | Tognola | |
| 3,463,946 A | 8/1969 | Zimmerman | |
| 3,465,161 A | 9/1969 | Cutkosky | |
| 3,483,759 A | 12/1969 | O'Sullivan, Jr., et al. | |
| 3,553,726 A | 1/1971 | Zimmerman | |
| 3,633,053 A | 1/1972 | Peters | |
| 3,746,937 A | 7/1973 | Koike | |
| 3,963,948 A | 6/1976 | Bratkowski et al. | |
| 3,980,908 A | 9/1976 | McClintock | |
| 3,984,707 A | 10/1976 | McClintock | |
| 4,158,811 A | 6/1979 | Li et al. | |
| 4,220,907 A | 9/1980 | Pappas | |
| 4,249,096 A | 2/1981 | Hickox | |
| 4,315,197 A | 2/1982 | Studer | |
| 4,342,920 A | 8/1982 | Bucknam | |
| 4,399,368 A | 8/1983 | Bucknam | |

(Continued)

OTHER PUBLICATIONS

Office Action from the United States Patent and Trademark Office, mailing date Feb. 3, 2011 for U.S. Appl. No. 12/399,448.

(Continued)

*Primary Examiner* — Carl H Layno
*Assistant Examiner* — Paula J Stice
(74) *Attorney, Agent, or Firm* — Curatolo Sidoti Co., LPA; Salvatore A. Sidoti; Vincent A. Cortese

(57) ABSTRACT

Disclosed is an implantable biomedical device that incorporates an electrical energy generator. The electrical energy generator harvests kinetic energy from voluntary motor activity of a human or animal and converts the kinetic energy to usable electrical energy which is used to power the biomedical device. In certain embodiments, the electrical energy generator includes a housing, an electrical conductor, an electromagnetically active mass, springs connecting the mass to the housing, and electrically circuitry to generate a usable source of electrical power for the biomedical device.

30 Claims, 2 Drawing Sheets

(56) References Cited

U.S. PATENT DOCUMENTS

| | | |
|---|---|---|
| 4,454,426 A | 6/1984 | Benson |
| 4,473,751 A | 9/1984 | Rombach et al. |
| 4,484,082 A | 11/1984 | Bucknam |
| 4,583,027 A | 4/1986 | Parker et al. |
| 4,649,283 A | 3/1987 | Berchowitz et al. |
| 4,754,644 A | 7/1988 | Valentini |
| 4,924,123 A | 5/1990 | Hamajima |
| 5,347,186 A | 9/1994 | Konotchick |
| 5,434,549 A | 7/1995 | Hirabayashi et al. |
| 5,503,314 A | 4/1996 | Fiscus |
| 5,564,612 A | 10/1996 | Gregory |
| 5,578,877 A | 11/1996 | Tiemann |
| 5,723,789 A | 3/1998 | Shannon |
| 5,762,243 A | 6/1998 | McMaster et al. |
| 5,762,251 A | 6/1998 | Gleason |
| 5,818,132 A | 10/1998 | Konotchick |
| 5,904,282 A | 5/1999 | Gleason |
| 5,965,964 A | 10/1999 | Skinner et al. |
| 5,975,714 A | 11/1999 | Vetorino et al. |
| 6,142,395 A | 11/2000 | Reiter |
| 6,170,767 B1 | 1/2001 | Herold et al. |
| 6,218,921 B1 | 4/2001 | Eberts et al. |
| 6,236,123 B1 | 5/2001 | Pinkerton |
| 6,619,523 B1 | 9/2003 | Duckworth |
| 6,637,631 B2 | 10/2003 | Lafoux et al. |
| 6,705,085 B1 | 3/2004 | Braithwaite et al. |
| 6,770,988 B2 | 8/2004 | Denne |
| 6,809,427 B2 | 10/2004 | Cheung et al. |
| 6,809,434 B1 | 10/2004 | Duncan et al. |
| 6,812,583 B2 | 11/2004 | Cheung et al. |
| 6,812,597 B2 | 11/2004 | McGill et al. |
| 6,815,847 B2 | 11/2004 | Duncan et al. |
| 6,853,103 B2 | 2/2005 | Moriyasu |
| 6,864,647 B2 | 3/2005 | Duncan et al. |
| 6,873,067 B2 | 3/2005 | Ichii et al. |
| 6,914,351 B2 | 7/2005 | Chertok |
| 6,936,937 B2 | 8/2005 | Tu et al. |
| 6,952,060 B2 | 10/2005 | Goldner et al. |
| 6,958,553 B2 | 10/2005 | Ichii et al. |
| 6,982,497 B2 | 1/2006 | Rome |
| 7,015,613 B2 | 3/2006 | Lilie et al. |
| 7,064,461 B2 | 6/2006 | Razzaghi |
| 7,124,720 B2 | 10/2006 | Liang et al. |
| 7,132,597 B2 | 11/2006 | Hosler |
| 7,148,583 B1 | 12/2006 | Shau et al. |
| 7,249,579 B2 | 7/2007 | Liang et al. |
| 7,285,878 B2 | 10/2007 | McGill et al. |
| 7,288,860 B2 | 10/2007 | Cheung et al. |
| 7,345,372 B2 | 3/2008 | Roberts et al. |
| 7,439,641 B2 | 10/2008 | Ogino et al. |
| 7,474,018 B2 | 1/2009 | Shimizu et al. |
| 7,498,682 B2 * | 3/2009 | Lemieux ............... 290/1 R |
| 7,692,320 B2 * | 4/2010 | Lemieux ............... 290/1 R |
| 7,712,174 B2 | 5/2010 | Shimizu et al. |
| 2003/0155771 A1 * | 8/2003 | Cheung et al. ......... 290/1 R |
| 2004/0100100 A1 | 5/2004 | Wilson |
| 2004/0104625 A1 | 6/2004 | Wakuda et al. |
| 2004/0150277 A1 | 8/2004 | Moriyasu |
| 2004/0155467 A1 | 8/2004 | Cheung et al. |
| 2004/0222637 A1 | 11/2004 | Bednyak |
| 2004/0222638 A1 | 11/2004 | Bednyak |
| 2004/0251748 A1 | 12/2004 | Inagaki et al. |
| 2004/0251750 A1 | 12/2004 | Cheung et al. |
| 2005/0211199 A1 | 9/2005 | Liang et al. |
| 2005/0211200 A1 | 9/2005 | Liang et al. |
| 2005/0279300 A1 | 12/2005 | Liang et al. |
| 2006/0192386 A1 | 8/2006 | Rome |
| 2007/0131185 A1 | 6/2007 | Liang et al. |
| 2007/0158946 A1 | 7/2007 | Annen et al. |
| 2007/0158947 A1 | 7/2007 | Annen et al. |
| 2007/0210580 A1 | 9/2007 | Roberts et al. |
| 2008/0036303 A1 | 2/2008 | Stevens |
| 2008/0074083 A1 * | 3/2008 | Yarger et al. ............ 320/137 |
| 2008/0174187 A1 | 7/2008 | Erixon et al. |
| 2008/0217926 A1 | 9/2008 | Lemieux |
| 2008/0284258 A1 | 11/2008 | Spratte et al. |
| 2009/0051229 A1 | 2/2009 | Shau |
| 2009/0058201 A1 | 3/2009 | Brennvall |
| 2009/0121493 A1 | 5/2009 | Lemieux |
| 2009/0121494 A1 | 5/2009 | Lemieux |
| 2009/0146508 A1 | 6/2009 | Peng et al. |
| 2009/0278358 A1 | 11/2009 | Lemieux |
| 2009/0295253 A1 | 12/2009 | Yarger et al. |
| 2009/0295520 A1 | 12/2009 | Yarger et al. |

OTHER PUBLICATIONS

English language abstract and machine translation of JP 2005-94832; Publication Date: Apr. 7, 2005; Applicant: Sony Corp.

International Search Report and Written Opinion, for PCT International Patent Application No. PCT/US2011/020361 corresponding to U.S. Appl. No. 12/985,777.

International Search Report and Written Opinion, for PCT International Patent Application No. PCT/US2011/020363 corresponding to U.S. Appl. No. 12/985,811.

* cited by examiner

IMPLANTABLE BIOMEDICAL DEVICE INCLUDING AN ELECTRICAL ENERGY GENERATOR

CROSS REFERENCE TO RELATED APPLICATIONS

This application claims the benefit of the filing date under 35 U.S.C. §119(e) of U.S. Provisional Application For Patent No. 61/034,651 filed on Mar. 7, 2008, which is hereby incorporated by reference in its entirety.

TECHNICAL FIELD

A medical device, such as an implantable medical device, which incorporates an electrical energy generator is disclosed. The electrical energy generator captures mechanical energy imparted to the device from movement and the converts the captured mechanical energy into electrical energy. The generated electrical energy is used to provide power to a wide variety of biomedical devices.

BACKGROUND

Mechanical energy comprises a number of forms of energy including, but not limited to kinetic energy. Mechanical energy is manifested in the bodies of humans and animals as a result of their physical processes. Such physical processes include voluntary body movements. Amongst voluntary body movements are gait processes. Gait activities include stepping, walking, running, climbing, jumping, and similar activities. Other voluntary body movements include grasping, reaching, shaking, swinging, stretching, etc. All voluntary body movements are manifested as motion of body members having mass so that all voluntary motor activities develop kinetic energy. Further, voluntary motor activities may impart kinetic energy to peripheral masses engaged with a moving body.

It is sometimes desirable to convert mechanical energy to electrical energy. An example is the conversion of kinetic energy into electrical energy as the kinetic energy of a mass moves a magnetic field relative to a conductive coil thereby converting the kinetic energy of the mass to electrical energy by action of electromagnetic induction.

Devices to convert the kinetic energy manifested in the bodies and peripheral masses engaged with the bodies of humans as a result of their physical processes into electrical energy are not well-developed.

Modern implanted biomedical devices included such devices as cardiac pacemakers and defibrillators, and neurostimulators. These devices rely on traditional sources of electrical power and therefore have a limited useful power source. Accordingly, such implantable biomedical devices would benefit from a device that can provide a sustainable source of electrical energy.

Accordingly, it is desirable to provide a device to harvest kinetic energy imparted by voluntary motor activities and convert the harvested mechanical energy into electrical energy to power implantable medical devices.

DETAILED DESCRIPTION

Figure 1:
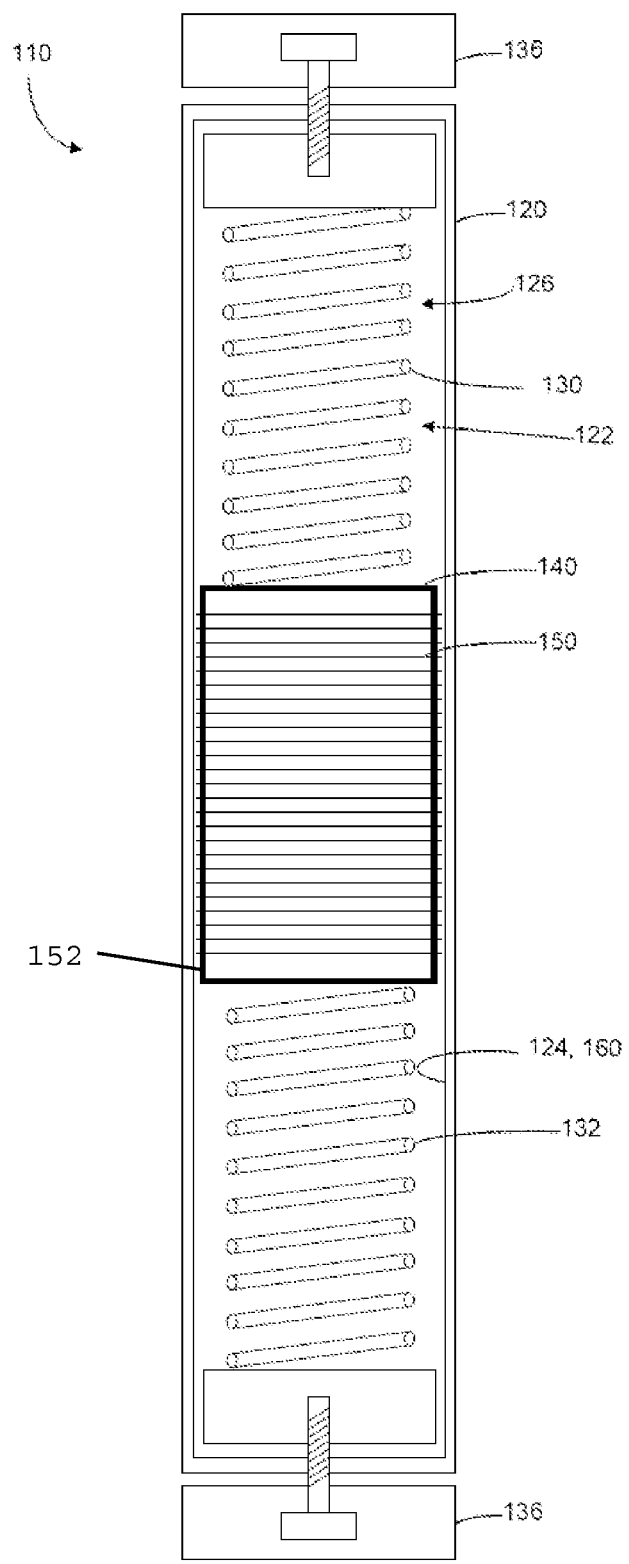
FIG. 1 is a perspective view of one illustrative embodiment of the electrical energy generator.

Provided is an implanatable biomedical device that is in electrical connection with an energy generator that is capable of generating a usable source of electrical energy from harvested energy by electromagnetic induction. According to certain embodiments, the electrical energy generator includes a housing having a longitudinal axis, an interior cavity, an interior cavity surface, and an exterior surface, an electrically conductive material engaged about at least a portion of said exterior surface of said housing and extending along at least a portion of said longitudinal axis, an electromagnetically active mass positioned within said housing reciprocally movable along at least a portion of said longitudinal axis and at least one spring for engaging the mass and the housing.

According to illustrative embodiments, the electromagnetically active mass is constrained within said housing to substantially prevent non-reciprocating motion of said electromagnetically active mass within said housing.

According to certain embodiments, the electrical energy generator includes a first spring having first and second ends, wherein one end is engaged with said housing and one end is engaged with said electromagnetically active mass, and a second spring having first and second ends, wherein one end is engaged with said housing and one end is engaged with said electromagnetically active mass.

According to other embodiments, the electrical energy generator that is in electrical connection with implantable biomedical device includes means to mitigate motion retardation of said electromagnetically active mass within the housing.

According to other embodiments, the mechanical energy harvester includes a housing having a longitudinal axis, electrically conductive material engaged about at least of portion of the exterior surface of said housing and extending along at least a portion of said longitudinal axis, an electromagnetically active mass positioned within said housing, said mass reciprocally movable along at least a portion of said longitudinal axis, a first spring having first and second ends, wherein one end is engaged with said housing and one end in engaged with said electromagnetically active mass, a second spring having first and second ends, wherein one end is engaged with said housing and one end is engaged with said electromagnetically active mass, and a means to mitigate motion retardation of said electromagnetically active mass within the housing.

According to further embodiments, the electrical energy generator that is in electrical connection with the implantable biomedical device includes a housing having a longitudinal axis, an interior cavity, an interior cavity surface, and an exterior surface, an electrically conductive material engaged about at least a portion of said exterior surface of said housing and extending along at least a portion of said longitudinal axis, an electromagnetically active mass positioned within said housing reciprocally movable along at least a portion of said longitudinal axis, a first spring having first and second ends, wherein one of said ends is engaged with said electromagnetically active mass, and a second spring having first and second ends, wherein one of said ends is engaged with said electromagnetically active mass, and at least one spring deflection adjustor engaged with said housing and at least one of said springs.

The electrical energy generator includes a housing, a coil of electrically conductive material, a reciprocally movable electromagnetically active mass, springs connecting the mass to either the housing or to adjustment means engaged with said housing, and, optionally, means for constraining nonlinear motion of the electromagnetically active mass, and/or means of mitigating motion retardation of the electromagnetically active mass within any existing housing atmosphere.

Kinetic energy is manifested in the bodies of animals and humans, as a result of different voluntary motor activities. Voluntary motor activities include, for example, gait processes, leg movements, arm movements, head movements, torso movements, and the like. Kinetic energy is also manifested in the objects or masses that are moved by a human or animal in the course of transporting them. Some voluntary motor activities, such as human walking gait, are rhythmic activities which have a predictable frequency or periodicity. In the case of human walking gait, the predictable frequency is approximately 2 Hz.

An electrical energy generator for harvesting kinetic energy and converting the harvested kinetic energy developed or imparted by voluntary motor activities into electrical energy is provided. The electrical energy generator generally comprises a housing, an induction coil, an electromagnetically active mass movable in a reciprocating manner relative to the housing, and at least one spring engaging the electromagnetically active mass to the housing.

According to certain illustrative embodiments, the electrical energy generator generally comprises a housing, an induction coil, an electromagnetically active mass movable in a reciprocating manner relative to the housing, a first spring engaged with the mass and the housing, and a second spring engaged with the mass and the housing.

According to further illustrative embodiments, the electrical energy generator comprises a housing, an induction coil, an electromagnetically active mass movable in a reciprocating manner relative to the housing, a first spring engaged with the mass and the housing, a second spring engaged with the mass and the housing, wherein the electromagnetically active mass is constrained within the housing to minimize or otherwise substantially prevent non-reciprocating movement of the mass.

According to other illustrative embodiments, the electrical energy generator comprises a housing, an induction coil, an electromagnetically active mass movable in a reciprocating manner relative to the housing, a first spring engaged with the mass and the housing, and a second spring engaged with the mass and the housing, and means of mitigating motion retardation of the electromagnetically active mass within the housing.

According to additional illustrative embodiments, the electrical energy generator comprises a housing, an induction coil, an electromagnetically active mass movable in a reciprocating manner relative to the housing, a first spring engaged with the mass and the housing, and a second spring engaged with the mass and the housing, and at least one spring deflection adjustor.

It should be noted that the electrical energy generator may include a combination of two or more of means for constraining the non-reciprocating movement of the electromagnetically active mass within the housing, means for mitigating motion retardation of the electromagnetically active mass within the housing, and at least one spring deflection adjustor.

The device harvests mechanical energy and converts the harvested mechanical energy into electrical energy. By harvesting mechanical energy from the reciprocating mass and converting it into electrical energy, the device acts as a linear electrical generator. The generated electrical energy may be used to power a wide variety of implantable biomedical devices, such as, without limitation, cardiac pacemakers, cardiac defibrillators, neurostimulators and any other implantable medical device.

The housing of the device may comprise any suitable structure, capsule, container, or vessel that is capable of engaging the other components of the electrical energy generator. The housing general includes a longitudinal axis, an exterior surface, an interior cavity, and an interior surface. Without limitation, according to certain embodiments, the housing comprises an elongated cylinder or tube having an interior cavity or volume.

The housing may be constructed of any material that can support the engagement of device components and that does not interfere with the harvest of mechanical energy or conversion of the mechanical energy into electrical energy. Without limitation, suitable material that may be used to construct the housing of the device comprises metal, metal alloys, plastic, glass, composite materials, or combinations thereof.

The housing may be provided as an open container, such that the interior of the housing is in communication with the external environment surrounding the housing. According to embodiments in which the housing is open, the means of communication with the environment surrounding the housing may include apertures, holes, vents, slots, perforations, or like structure located within the wall of the housing, thereby providing communication between the interior cavity of the housing and the external environment. In open embodiments, the housing atmosphere is generally substantially identical to the surrounding environmental atmosphere.

According to other embodiments, the housing comprises a closed structure such that the interior of the housing is substantially isolated from the environment surrounding the housing. According to embodiments including a closed housing, the housing atmosphere need not be substantially identical to the surrounding external environmental atmosphere. For example, without limitation, the housing atmosphere may comprise air, nitrogen, a Nobel gas, mineral oil, vegetable oil, water, saline, substantial vacuum, a ferrofluid, or combinations thereof.

The device includes an electrically conductive material that is engaged about at least a portion of the exterior surface of said housing. Without limitation, the electrically conductive material may be provided in the form of an induction coil. The induction coil may include an armature, inductor, wire coil, or any other looped electrically conductive material. A change in a local magnetic field produces a current within and a potential across an induction coil. Because the induction coil is engaged about the housing and extends along a portion of the axis of the housing a change in a magnetic field proximal to that portion of the housing engaged with the induction coil produces a current within and a potential across the induction coil.

The device includes at least one spring engaging the electromagnetically active mass to the housing. The springs generally have opposite first and second ends, and are engaged at one end with the housing and at the other end with the electromagnetically active mass. A spring is any component which produces a restorative force in response to its displacement. Certain springs produce restorative forces directly proportional to their displacement. Springs which produce restorative forces directly proportional to their displacement are springs which obey Hooke's Law. A spring accumulates mechanical energy in the form of potential energy as work is done upon it and releases it as the above-referenced restorative force. The relationship between the restorative force and the displacement is the spring coefficient. In springs which obey Hooke's Law, the spring coefficient is substantially constant.

According to certain illustrative embodiments, the electrical energy generator includes first and second springs that obey Hooke's Law. These first and second springs are attached to opposite ends of the device housing and to opposite ends of the electromagnetically active mass that is located within the device housing. Because these springs substantially obey Hooke's Law, the springs are considered to be harmonic oscillators and can provide a natural frequency. In certain circumstances, however, it may be advantageous to utilize springs that possess stiffening spring characteristics such that at the end of travel, there would be no need to incorporate any rebound means with the device.

In certain embodiments, the springs included in the device comprise coil springs. A coil spring is a type of torsion spring. A coil spring comprises an elastic material formed into a helix, or spiral, or spiral helix having two opposite ends. The coil springs may comprise either compression springs or extension springs.

A spring pre-load is a load that exists in the spring prior to deflection of the spring from some initial state. As used herein, pre-load of a spring refers to the load in the spring in the unexcited device in which the electromagnetically active mass is at rest. The device may also include a suitable means for adjusting the deflection or spring pre-load on the coil springs. A means of adjusting spring pre-load comprises any component which introduces or removes a load, tension or compression of an installed spring, usually in the unexcited device. Introduction or removal of a load of an installed spring may be done by adjusting the deflection of the spring. In certain embodiments the means of adjusting spring pre-load and deflection comprises a movable member with which the spring to have its pre-load and deflection adjusted is engaged. In such embodiments, the region of engagement between the spring and the member is movable with respect to the housing. In certain embodiments, the moveable member comprises a threaded member. Threaded members may comprise screws, bolts, and threaded bushings. In certain embodiments the threaded member is engaged with a counterpart threaded receiver that is substantially fixed to or integral to the housing. One illustrative method of moving the point of engagement between the spring and the threaded member with respect to the housing is by advancement or retraction of the threaded member by rotating the threaded member with respect to the threaded receiver. As the threaded member is rotated, the threaded member and the region of engagement between the spring and the member moves helically with respect to the threaded receiver, and thereby moves helically with respect to the housing. The amount of movement will be equal to the product of the thread pitch and the number of rotations made. The amount of change in the load will be equal to the product of the amount of movement and the spring coefficient.

In certain embodiments, the springs comprise a first spring having a first end engaged with the housing and a second end engaged with said electromagnetically active mass, and a second spring having a first end engaged with the housing and a second end engaged with said electromagnetically active mass. In certain embodiments, the springs comprise a first spring having a first end engaged with a first threaded member and a second end engaged with said electromagnetically active mass, and a second spring having a first end engaged with a second threaded member and a second end engaged with said electromagnetically active mass.

As used in this disclosure, "electromagnetically active" refers to a mass that is capable of affecting a magnetic field. Electromagnetically active components include, but are not limited to, permanent magnets, electromagnets, inductors, and materials having magnetic permeability. The electrical energy generator may comprise one or more electromagnetically active components to affect a desired magnetic field.

An electromagnetically active mass may be any electromagnetically active component which also has mass. An electromagnetically active mass is capable of producing a magnetic field or bending the flux lines of a magnetic field. Electromagnetically active masses capable of producing a magnetic field comprise permanent magnets, electromagnets and the like. Electromagnetically active masses capable of bending the flux lines of a magnetic field may also comprise materials having magnetic permeability. In certain embodiments, the materials having magnetic permeability are materials which have a high permeability. Without limitation, materials which have a high permeability comprise iron, nickel, chromium, and like materials. In certain embodiments, an electromagnetically active mass may comprise metal, metal alloys, ceramics, and mixtures thereof.

The electromagnetically active mass is positioned within the interior cavity of the housing and is engaged with each of two coil springs, with each of the coil springs being further engaged with the housing. The manner of engagement of the springs and mass allows the electromagnetically active mass to move in a reciprocating manner with respect to the housing. The electromagnetically active mass defines a volume which is swept out by the electromagnetically active mass as it moves. The volume which is swept out by the electromagnetically active mass as it moves is at least a portion of the volume of the interior cavity of the housing.

The shape of the electromagnetically active mass can vary greatly, and there is no particular shape to which the electromagnetically active mass must be limited. In certain embodiments, the electromagnetically active mass comprises an axisymmetric shape. In certain embodiments, the electromagnetically active mass comprises substantially cylindrical shape.

In certain embodiments, the electromagnetically active mass comprises at least one through-hole. In certain embodiments the electromagnetically active mass is a substantially cylindrical axisymmetric mass comprising a through-hole.

A guidance means comprises any component that comprises a portion of the housing, or that is engaged to or integral with, the housing and has a guidance surface for the electromagnetically active mass over at least a portion of the path described by the mass as it moves. In certain embodiments, the material of the guidance means comprises metal, plastic, glass, composite materials, or combinations thereof. In certain embodiments the guidance surface of the guidance means comprises a surface coating. The surface coating may comprise metal, plastic, glass, composite materials, or combinations thereof. In certain embodiments the guidance means, or the guidance surface of the guidance means, may comprise PTFE, PEEK, or oil-impregnated bronze. The guidance surface of the guidance means may substantially coincide with at least a portion of the surface of the volume swept out by the electromagnetically active mass as it moves. According to certain embodiments, the guidance means guides the mass by providing restorative forces to the mass in directions substantially normal to the surface of the means in response to contact between the mass and the means. These restorative forces are referred to as "normal forces". By providing such restorative forces, the guidance means impedes motion of the mass in directions normal to the means. In certain embodiments, the mass may be engaged with the guidance means during all portions of the motion of the mass. In certain embodiments, the mass is constrained by the guidance means to minimize substantially all motion of the mass other than linear reciprocation, such that motion of the mass is limited to substantially linear reciprocation. There will exist a coefficient of friction determined by the material of the guidance surface and the material of the electromagnetically active mass which contacts the material of the guidance surface. The product of the coefficient of friction and the normal forces defines the magnitude of friction forces between the mass and the means which retard the motion of the mass. In certain embodiments, the coefficient of friction is selected to be very low in order to minimize the magnitude of friction forces.

In certain embodiments, the guidance surface of the guidance means comprises the interior surface of the housing. In certain embodiments, in which the electromagnetically active mass comprises at least one through-hole, the guidance means comprises a shaft or rod passing through a through-hole and along which said electromagnetically active mass moves as it reciprocates.

The electrical energy generator may further comprises a means of mitigating motion retardation of the electromagnetically active mass by the housing atmosphere. The housing atmosphere comprises a fluid, wherein such fluid may be a gas or a liquid. Fluids are known to retard the motion of materials through them. In certain circumstances, the housing atmosphere will retard the motion of the electromagnetically active mass through the housing atmosphere.

One type of retardation of the motion of the electromagnetically active mass is by viscous effects. Viscous effects which retard motion appear whenever a body moves through a fluid having a positive viscosity. One means of mitigating motion retardation by viscous effects is by rarification or evacuation of the housing atmosphere. In certain embodiments, the housing atmosphere comprises a gas at sub-atmospheric pressure, such that the housing atmosphere is reduced, rarified, or evacuated to the point that it comprises a substantial vacuum.

Retardation of the motion of the electromagnetically active mass may occur by pressure differentials. Pressure differentials may be created by motion of an object within, and in close clearance to, a closed housing. In certain embodiments, the electromagnetically active mass may be engaged in very close tolerance to a closed housing. One means of mitigating motion retardation by pressure differentials is by the inclusion of apertures, flow-paths, flutes, or ducts to permit flow from the region into which the mass is moving and to the region from which the mass is moving. In certain embodiments, the interior surface of the housing may comprise longitudinal flutes to permit flow of the fluid comprising the housing atmosphere from one region of the interior cavity to another region of the interior cavity. In certain embodiments the electromagnetically active mass may comprise one or more through-holes or flutes which permit flow of the fluid comprising the housing atmosphere around, across, or through the mass.

According to certain embodiments, the electrical energy generator may further comprise an electromagnetically active shroud that is engaged with the housing and at least partially covering the induction coil. In certain embodiments, the electrical energy generator comprises an electromagnetically active shroud that is engaged with the housing which at least partially covers said housing. In certain embodiments, the electrical energy generator comprises an electromagnetically active shroud that is engaged with the housing which partially covers said housing. In certain embodiments, the electrical energy generator may comprise an electromagnetically active shroud that is engaged with the housing which fully covers said housing. In certain embodiments the electromagnetically active shroud may comprise a permanent magnet. In certain embodiments, the electromagnetically active shroud comprises an unmagnetized material having magnetic permeability. In embodiments in which the electromagnetically active mass comprises an unmagnetized material having magnetic permeability, the device will further comprise an electromagnetically active shroud which comprises a permanent magnet. In certain embodiments in which the electromagnetically active mass comprises a permanent magnet, the device comprises an electromagnetically active shroud comprising an unmagnetized material having magnetic permeability.

The electrical energy generator comprises an electromagnetically active mass which reciprocates within the housing. Exciting forces acting on the housing excite the mass causing it to move within the housing in a reciprocating manner which is substantially harmonic. Further, the electrical energy generator comprises components which remove mechanical energy from the mass when it is in motion, thereby electromagnetically damping it. Because of these properties, certain embodiments of the electrical energy generator may be described as a substantially harmonic damped oscillator. It should be noted that the damping of the energy from the mass may comprise critically damping, greater than critically damping or less than critically damping. According to certain illustrative embodiments, the damping of the energy from the mass comprises less than critical damping. According to yet further embodiments, the damping of the energy of the mass may be variable.

When a driving force is acting on the electrical energy generator, according to certain embodiments, the device behaves as a substantially harmonic driven, damped oscillator. Harmonic oscillators have a fundamental or natural frequency which is a function of oscillating mass and spring coefficient. Because the mass of the electromagnetically active mass is determinable and because the spring coefficient of the spring is determinable, the natural frequency of the device is also determinable. The selection of the mass or spring coefficient or both to adjust the natural frequency of the device is referred to herein as "tuning". That is, the natural frequency of the device may be tuned by selection of the mass or the spring coefficient or both.

Because the mass, by definition, has inertia, an exciting force directed to the device along a direction which is not perpendicular to the axis of reciprocation, causes the housing to be displaced to a greater extent than the mass is caused to be displaced. This difference in displacement causes some of the exciting kinetic energy imparted by the action of the exciting force acting over said displacement to be absorbed by the electromagnetically active mass, the springs and the induction coil.

Because the electrical energy generator includes an electromagnetically active mass, a spring, and an induction coil, when set into motion, the device can behave as a damped vibrating system and will vibrate until it dissipates the exciting energy. The natural frequency or frequencies of the harvester can be predetermined. Without limitation, in certain embodiments, the electrical energy generator behaves as a substantially harmonic oscillator having one natural frequency. The level of damping in the device can be predetermined.

The certain illustrative embodiments of the device will be described in further detail with respect to the Figures. It should be noted that the electrical energy generator should not be limited to the illustrative embodiments depicted by the Figures.

As shown in FIG. 1, the device (110) comprises a housing (120) which comprises an elongated circular cross-section tube having first and second ends. The housing (120) comprises an internal cavity (122) defined by the tube, an interior surface (124) and an atmosphere (126). The device further comprises a first spring (130) having a first end and a second end. Spring (130) comprises an extension coil spring having the first end attached to the first end portion of the housing (120). The device further comprises a second spring (132) having a first end and a second end. Spring (132) comprises an extension coil spring having the first end attached to the first end portion of the housing (120). The device (110) further comprises an electromagnetically active mass (140) engaged with each of springs 130 and 132. The electromagnetically active mass (140) is moveable within said housing (120). The electromagnetically active mass (140) moves in a reciprocating manner along a path constrained by a guidance means (160), which is, in the embodiment shown, the interior surface (124) of the housing (120). Movement of electromagnetically active mass (140) relative to the housing (120) causes motion of said mass-engaged second end of each spring (130 and 132) with respect to said housing-engaged first end of each spring (130 and 132) such that the motion of the electromagnetically active mass (140) relative to the housing (120) results in deflection of the springs (130 and 132). The device (110) further comprises an induction coil (150) that is engaged about the exterior portion of the housing (120), and a shroud (152) covering a portion of induction coil (150).

Figure 2:
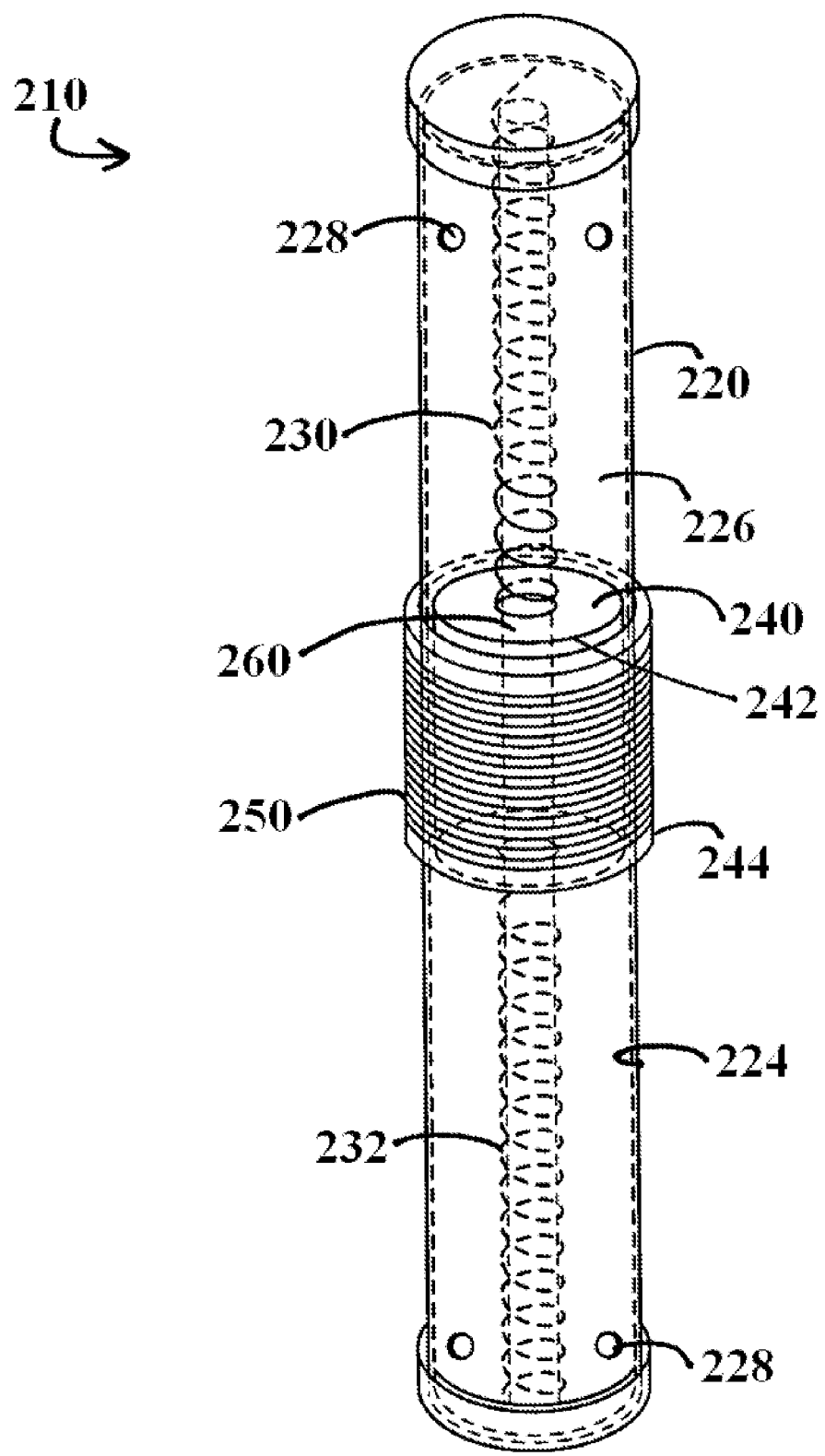
FIG. 2 is a perspective view of another illustrative embodiment of the electrical energy generator.

As shown in FIG. 2, the device (210) comprises a housing (220) which comprises an elongated circular cross-section tube having a first and second ends. The housing (220) comprises an internal cavity (222) defined by the tube, an interior surface (224), an atmosphere substantially similar to the ambient atmosphere (226), and apertures (228) in the housing which provide communication between the exterior environment and the interior cavity (222) of housing (220). The device further comprises a first spring (230) having a first end and a second end. Spring (230) comprises a compression coil spring having said first end attached to the first end portion of the housing (220). The device further comprises a second spring (232) having a first end and a second end. Spring (232) comprises a compression coil spring having said first end attached to the first end portion of the housing (220). The device (210) further comprises an electromagnetically active mass (240) engaged with each spring (230 and 232). The electromagnetically active mass (240) is moveable within said housing (220). The mass (240) moves in a reciprocating manner along a path constrained by a guidance means (260) which is, in the embodiment shown, an elongated rod engaged at either end with housing (220) and passing through a through-hole (242) in the electromagnetically active mass (240). Movement of electromagnetically active mass (240) relative to the housing (220) causes motion of said mass-engaged second end of each spring (230 and 232) with respect to said housing-engaged first end of each spring (230 and 232) such that the motion of the mass (240) relative to the housing (220) results in deflection of the springs (230 and 232). The harvester (210) further comprises an induction coil (250) engaged about the exterior surface of the housing (220). In certain embodiments, the harvester (210) may further include a shroud (244) which is engaged with the housing (220) and at least partially covers the induction coil (250) and/or the housing (220).

The electrical energy generator may be implanted in the body of a subject along with the implanted biomedical device. Alternatively, the electrical energy generator, while still in electrical communication with the implanted biomedical device, may be located outside of the body of a subject. In certain embodiments the electrical energy generator is located outside of the body of a subject, it may be engaged with a worn item or a carried item. Worn items comprise clothing, such as a hat, belt, shirt, pants, dress, skirt, sweater, sweatshirt, jacket and the like. Protective gear, includes without limitation body armor, life vest, personal flotation devices and the like. Carrying items include without limitation backpacks, waist-packs, field-packs, medical packs, bags, toolbags, book-bags, purses, briefcases, holsters, sheaths and the like.

In embodiments in which the electrical energy generator is engaged with a worn item, the worn item is excited by exciting forces imparted from the wearer, and the electrical energy generator is excited by exciting forces imparted from the worn item. The engagement of the electrical energy generator with the worn item may be fine such that the device is substantially immobile relative to the worn carrying device; flexible or soft such that there is a great deal motion of the device relative to the worn item; or somewhere in between.

For purposes of illustration and without limitation a common excitation frequency for walking is about 2 Hz. This information may be used to predetermine an appropriate natural frequency of the electrical energy generator. Depending upon the embodiment and desired operational characteristics, it may be desirable to have one or more of the natural frequencies of the device similar to one or more of the operational frequencies of the source of the excitation kinetic energy; or dissimilar to one or more of the expected operational frequencies of the source of the excitation kinetic energy by some predetermined amount. In certain embodiments, one natural frequency of the device is predetermined to correspond to the steady state harmonic motion of the gait of the human or animal by which it is carried or worn.

While the combination of an implantable biomedical device and electrical energy generator has been described in connection with various illustrative embodiments, as shown in the Figures, it is to be understood that other similar embodiments may be used or modifications and additions may be made to the described embodiments for performing the same functions. Therefore, the combination should not be limited to any single embodiment, but rather construed in breadth and scope in accordance with the recitation of the appended claims.

I claim:

1. A combination comprising an implantable biomedical device and an electrical energy generator, wherein said electrical energy generator is capable of generating electrical energy from kinetic energy by electromagnetic induction, said electrical energy generator being in electrical connection with said implantable biomedical device, wherein said electrical energy generator comprises:
   a housing having a longitudinal axis, an interior cavity and an interior cavity surface, and an exterior surface;
   electrically conductive material positioned about at least a portion of said exterior surface of said housing and extending along at least a portion of said longitudinal axis of said housing;
   an electromagnetically active mass positioned within said housing reciprocally movable along at least a portion of said longitudinal axis of said housing; and
   guidance means to minimize or substantially prevent the non-reciprocating motion of said electromagnetically active mass within said housing, wherein said guidance means comprises a rod engaged with said housing and passing through said electromagnetically active mass.

2. The combination of claim 1, wherein said housing comprises a cylinder or tube.

3. The combination of claim 2, wherein said electrically conductive material comprises an induction coil.

4. The combination of claim 3, wherein the entirety of said electromagnetically active mass is adapted to pass through the entirety of said induction coil twice during a single reciprocation period.

5. The combination of claim 4, wherein said springs comprise coil springs.

6. The combination of claim 5, wherein said coil springs comprise extension springs.

7. The combination of claim 5, wherein said coil springs comprise compression springs.

8. The combination of claim 4, wherein said electromagnetically active mass comprises at least one permanent magnet.

9. The combination of claim 8, wherein said electrical energy generator further comprises a shroud at least partially covering said induction coil, said shroud having a high magnetic permeability.

10. The combination of claim 9, wherein said shroud comprises a ferromagnetic material.

11. The combination of claim 4, wherein:
said electromagnetically active mass does not comprise a permanent magnet; and
said electrical energy generator further comprises a shroud at least partially covering said induction coil, wherein said shroud comprises a permanent magnet.

12. The combination of claim 1, further comprising at least one spring deflection adjustor engaged with said housing and at least one of said first and second springs.

13. The combination of claim 12, wherein said spring deflection adjustor comprises:
a threaded receiver engaged with said housing; and
a threaded member rotatably engaged with said threaded receiver to permit helical motion of said threaded member with respect to said housing.

14. The combination of claim 12, wherein said housing comprises a cylinder or tube.

15. The combination of claim 14, wherein said electrically conductive material comprises an induction coil.

16. The combination of claim 15, wherein said first and second springs comprise coil springs.

17. The combination of claim 16, wherein said coil springs comprise extension springs.

18. The combination of claim 17, wherein said shroud comprises a ferromagnetic material.

19. The combination of claim 16, wherein said coil springs comprise compression springs.

20. The combination of claim 16, wherein the entirety of said electromagnetically active mass is adapted to pass through the entirety of said induction coil twice during a single reciprocation period.

21. The combination of claim 20, wherein said electromagnetically active mass comprises a permanent magnet.

22. The combination of claim 21, wherein said electrical energy generator further comprises a shroud at least partially covering said induction coil, said shroud having a high magnetic permeability.

23. The combination of claim 16 wherein:
said electromagnetically active mass does not comprise a permanent magnet; and
said electrical energy generator further comprises a shroud at least partially covering said induction coil, wherein said shroud comprises a permanent magnet.

24. The combination of claim 13, wherein said threaded member comprises male threaded shafts.

25. The combination of claim 13, wherein said threaded receiver comprises female threads integrally formed in said housing.

26. A combination comprising an implantable biomedical device and an electrical energy generator, wherein said electrical energy generator is capable of generating electrical energy from kinetic energy by electromagnetic induction, said electrical energy generator being in electrical connection with said implantable biomedical device, wherein said electrical energy generator comprises:
a housing having a longitudinal axis, an interior cavity and an interior cavity surface, and an exterior surface;
electrically conductive material positioned about at least a portion of said exterior surface of said housing and extending along at least a portion of said longitudinal axis of said housing;
an electromagnetically active mass positioned within said housing reciprocally movable along at least a portion of said longitudinal axis of said housing;
a first spring having first and second ends, wherein one of said ends is engaged with said housing and one of said ends is engaged with said electromagnetically active mass;
a second spring having first and second ends, wherein one of said ends is engaged with said housing and one of said ends is engaged with said electromagnetically active mass; and
at least one spring deflection adjustor engaged with said housing and at least one of said first and second springs;
wherein said spring deflection adjustor comprises a threaded receiver engaged with said housing and a threaded member rotatably engaged with said threaded receiver to permit helical motion of said threaded member with respect to said housing.

27. The combination of claim 26, wherein said electromagnetically active mass is constrained within said housing to minimize or substantially prevent non-reciprocating motion of said electromagnetically active mass within said housing.

28. The combination of claim 26, further comprising guidance means to minimize or substantially prevent the non-reciprocating motion of said electromagnetically active mass within said housing.

29. The combination of claim 28, wherein said guidance means comprises said interior cavity surface of said housing or a rod engaged with said housing and said electromagnetically active mass.

30. The combination of claim 26, wherein said housing comprises a cylinder or tube.

* * * * *